United States Patent [19]

Kawagishi et al.

[11] Patent Number: 4,931,588

[45] Date of Patent: Jun. 5, 1990

[54] COMPOUNDS USABLE IN A TONER FOR DEVELOPING ELECTROSTATIC LATENT IMAGES

[75] Inventors: Yoji Kawagishi, Kyoto; Shinichi Narita, Osaka; Takashi Kiriu, Osaka; Schunichiro Yamanaka, Osaka, all of Japan

[73] Assignee: Orient Chemical Industries, Ltd., Osaka, Japan

[21] Appl. No.: 292,329

[22] Filed: Sep. 15, 1989

Related U.S. Application Data

[62] Division of Ser. No. 852,994, Apr. 17, 1980, Pat. No. 4,826,749.

[30] Foreign Application Priority Data

Jun. 28, 1985 [JP] Japan ............................... 60-143380
Sep. 25, 1985 [JP] Japan ............................... 60-213140

[51] Int. Cl.$^5$ ............................................ C07C 87/30

[52] U.S. Cl. ...................................... 562/68; 562/70; 562/79

[58] Field of Search ........................ 562/68, 70, 79, 84

[56] References Cited

U.S. PATENT DOCUMENTS 4,654,175 3/1987 Lu et al. ................................ 562/84
4,684,596 8/1987 Bonser et al. ........................ 430/110

*Primary Examiner*—Nicky Chan

*Attorney, Agent, or Firm*—McGlew & Tuttle

[57] ABSTRACT

A salt forming compound represented by the formula

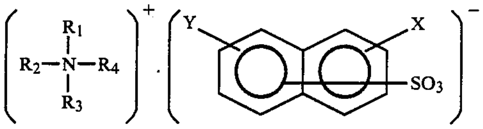

wherein $R_1$ is $C_1$–$C_8$ alkyl or benzyl, $R_2$ and $R_3$ are each $C_1$–$C_{18}$ alkyl, $R_4$ is $C_1$–$C_{18}$ alkyl or benzyl, X is hydroxyl or amino, and Y is hydroxyl or hydrogen and is not hydrogen when X is hydroxyl, usable in a toner for developing electrostatic latent images, e.g. comprising 0.5 to 5 parts by weight of the salt forming compound and 100 parts by weight of a resin.

8 Claims, No Drawings

COMPOUNDS USABLE IN A TONER FOR DEVELOPING ELECTROSTATIC LATENT IMAGES

This is a divisional application of application Ser. No. 852,994 filed Apr. 17, 1986, now U.S. Pat. No. 4,826,749.

BACKGROUND OF THE INVENTION

1. Field of the Invention

The present invention relates to a novel dry positively chargeable toner for developing electrostatic latent images for use in electrophotography, electrostatic recording, electrostatic printing, etc.

2. Description of the Prior Art

Electrostatic latent images can be developed into visible images by depositing a toner on the latent image by electrostatic attraction. Powder developers as well as liquid developers are widely used for developing electrostatic latent images. Powder developers can be divided generally into two-component developers and single-component developers. The two-component developer comprises a particulate toner having a mean particle size of 15 μm and prepared by dispersing a coloring agent, charge control agent, fluidizing agent and the like in a natural or synthetic resin, and a carrier of finely divided iron, ferrite or the like admixed with the toner and having a particle size of 100 to 200 μm. The latter single-component developer comprises only a particulate toner having a mean particle size of 15 μm and prepared by dispersing a coloring agent, charge control agent, fluidizing agent and the like in a natural or synthetic resin.

With the two-component developer, the toner is triboelectrically charged by the carrier and deposited on electrostatic latent images for development. The toners heretofore known and serving as single-component developers include those which are triboelectrically chargeable by a brushlike or platelike friction member having the same function as the carrier and serving as a substitute therefor. Further provided in recent years are toners which are triboelectrically chargeable by a dispersed finely divided magnetic material. These developing toners are charged positively or negatively in accordance with the polarity of the electrostatic latent image to be developed.

To enable the toner to retain the charge, it is also proposed to utilize the triboelectric chargeability of the resin used as the main component of the toner, but the toner so adapted is low in chargeability and has a great solid surface resistance value. Consequently the toner image obtained is prone to fogging and obscure. Although a toner is known in which a certain functional group is introduced into the resin to enable the toner to retain positive charges, the toner releases a disagreeable odor during thermal fixing due to the functional group and is subject to variations in the amount of charges retainable. The charge control agents presently used in the art for giving positive chargeability include the nigrosine dyes disclosed in Examined Japanese Patent Publication SHO 41-2427, etc., the quaternary ammonium salts disclosed in U.S. Pat. No. 3,565,654, etc. and polyamide resins disclosed in Examined Japanese Patent Publication SHO 53-13284.

However, many of these charge control agents heretofore used are colored and are therefore not suited to color toner compositions although useful for black toner compositions. Further the above-mentioned quaternary ammonium salts provided as colorless charge control agents are soluble in water, difficult to disperse uniformly in the toner and prone to uneven charging. Further even if the toner incorporating the agent has high chargeability immediately after preparation, the chargeability decreases exponentially functionally depending on the conditions under which the toner is stored, and this tendency becomes more pronounced when the toner is exposed to a high temperature and high humidity. To overcome these drawbacks, improvements have been made in charge control agents as disclosed, for example, in Unexamined Japanese Patent Publications SHO 56-11461, SHO 57-54953, SHO 57-119364, SHO 58-9154 and SHO 58-98742, etc. Despite these research efforts, nevertheless, a fully satisfactory charge control agent still remains to be developed.

SUMMARY OF THE INVENTION i We have conducted intensive research on compounds which are colorless, capable of giving positive charges to toners and satisfactory in dispersibility in resin components, have thermal stability at temperatures at which toner compositions can be satisfactorily kneaded in a molten state, and give toners chargeability which remains almost unchanged with time even when the toner is subjected to varying environmental conditions, and consequently developed a salt forming compound comprising a quaternary ammonium salt and a naphthalenesulfonic acid having substituents, the salt forming compound being represented by the formula

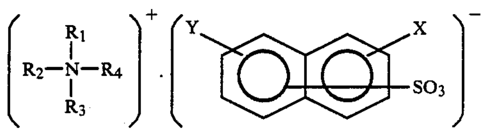

(I)

wherein $R_1$ is $C_1$–$C_8$ alkyl or benzyl, $R_2$ and $R_3$ are each $C_1$–$C_{18}$ alkyl, $R_4$ is $C_1$–$C_{18}$ alkyl or benzyl, X is hydroxyl or amino, and Y is hydroxyl or hydrogen and is not hydrogen when X is hydroxyl. We have found that this compound is colorless or pale colored to such an extent that it can be regarded as substantially colorless, thermally stable, highly amenable to pulverization, highly compatible with resins and useful as a charge control agent in preparing a toner which is uniformly chargeable and has outstanding durability against changes of environmental conditions. Thus, the present invention has been accomplished.

DETAILED DESCRIPTION OF THE INVENTION

The compound of the present invention represented by the formula (I) can be prepared from a quaternary ammonium salt represented by the formula

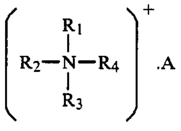

(II)

wherein $R_1$ is $C_1$–$C_8$ alkyl or benzyl, $R_2$ and $R_3$ are each $C_1$–$C_{18}$ alkyl, $R_4$ is $C_1$–$C_{18}$ alkyl or benzyl, and A is an anion, and a naphthalenesulfonic acid having substituents and represented by the formula

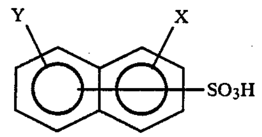

(III)

wherein X is hydroxyl or amino, and Y is hydroxyl or hydrogen and is not hydrogen when X is hydroxyl, by a known salt forming method.

Examples of useful quaternary ammonium salts represented by the formula (II) are tetramethylammonium chloride, benzyltrimethylammonium chloride, stearyltrimethylammonium chloride, benzyltriethylammonium chloride, benzyltributylammonium chloride, tetrabutylammonium bromide, dibenzyldimethylammonium chloride, benzyloctyldimethylammonium chloride and the like.

Examples of useful naphthalenesulfonic acids having substituents and represented by the formula (III) are 1,5-dihydroxynaphthalene-4-sulfonic acid, 1,7-dihydroxynaphthalene-3-sulfonic acid, 1,8-dihydroxynaphthalene-4-sulfonic acid, 2,3-dihydroxynaphthalene-6-sulfonic acid, 4-amino-1-naphthol-2-sulfonic acid, 5-amino-1-naphthol-3-sulfonic acid, 6-amino-1-naphthol-3-sulfonic acid, 8-amino-1-naphthol-5-sulfonic acid, 1-amino-2-naphthol-4-sulfonic acid, 1-amino-2-naphthol-6-sulfonic acid, 5-amino-2-naphthol-7-sulfonic acid, 8-amino-1-naphthalenesulfonic acid, 2-amino-1-naphthalenesulfonic acid, 4-amino-1-naphthalenesulfonic acid, 5-amino-1-naphthalenesulfonic acid, 6-amino-1-naphthalenesulfonic acid, 7-amino-1-naphthalenesulfonic acid, 5-amino-2-naphthalenesulfonic acid, 6-amino-2-naphthalenesulfonic acid, 8-amino-2-naphthalenesulfonic acid and the like.

SYNTHESIS EXAMPLE 1

Synthesis of benzyltripropylammonium-1,7-dihydroxynaphthalene-3-sulfonate

A 54 g quantity of 50% aqueous solution of benzyltripropylammonium chloride was diluted with 80 ml of water. A solution of 26.2 g of sodium 1,7-dihydroxynaphthalene-3-sulfonate in 500 ml of water was added dropwise to the dilution at room temperature with stirring. The mixture was then heated to about 80° C. and reacted for one hour. The reaction mixture was cooled to about 30° C. with stirring, filtered, washed with water and dried, giving 42 g of a light yellow powder, m.p. 228° to 232° C.

SYNTHESIS EXAMPLE 2

Synthesis of benzyltributylammonium-4-aminonaphthalene-1-sulfonate

A 62 g quantity of 50% aqueous solution of benzyltributylammonium chloride was diluted with 80 ml of water. A solution of 24.5 g of sodium 4-amino naphthalene-1-sulfonate in 500 ml of water was added dropwise to the dilution at room temperature with stirring. The mixture was then heated to about 80° C. and reacted for one hour. The reaction mixture was cooled to about 30° C. with stirring, filtered, washed with water and dried, affording 44 g of a white powder, m.p. 128° to 133° C.

Given below are examples of salt forming compounds of the present invention represented by the formula (I).

| No. | Compound | Appearance M.p. (uncorrected) |
|---|---|---|
| (1) | 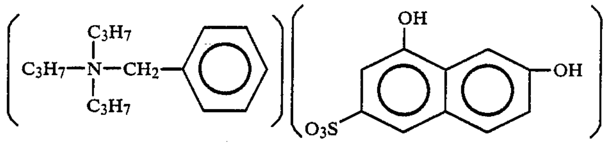 | Light yellow 228-232° C. |
| (2) | 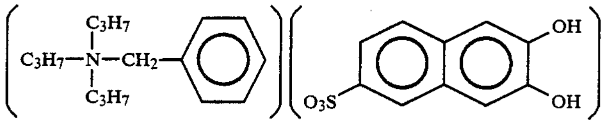 | Light yellow 248-251° C. |
| (3) | 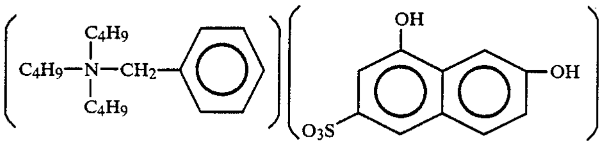 | White 225-228° C. |
| (4) | 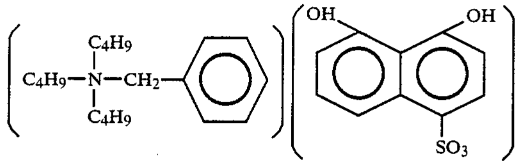 | White 240-243° C. |

-continued
| No. | Compound | Appearance M.p. (uncorrected) |
|---|---|---|
| (5) | 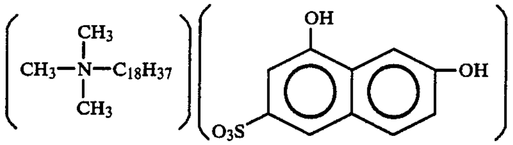 | Light brown 195-201° C. |
| (6) | 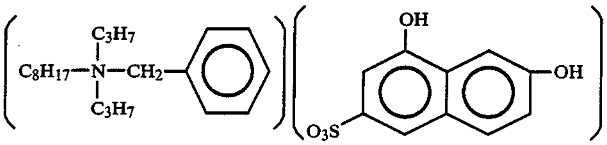 | Light yellow 226-232° C. |
| (7) | 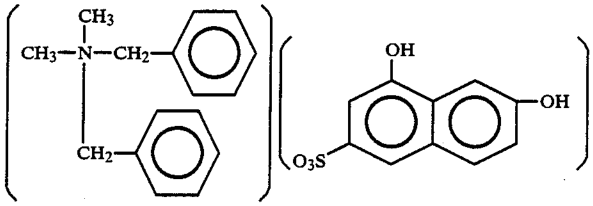 | Light yellow 238-241° C. |
| (8) | 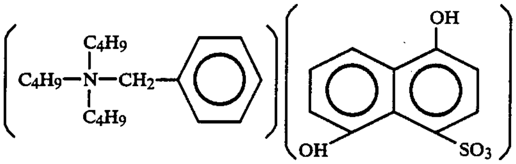 | White 215-220° C. |
| (9) | 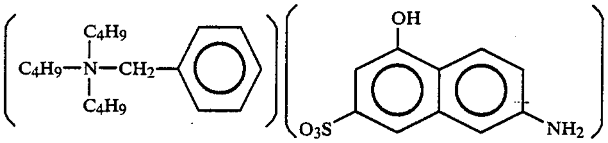 | White 135-138° C. |
| (10) | 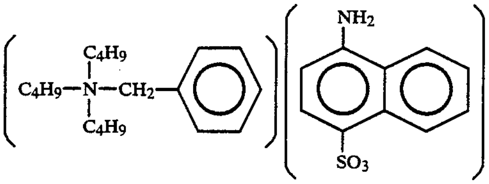 | White 128-133° C. |
| (11) | 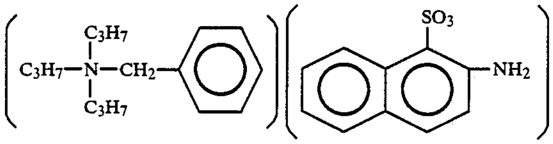 | Slightly brown 145-148° C. |
| (12) | 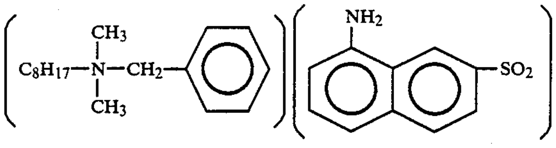 | Slightly brown 115-118° C. |

-continued

| No. | Compound | Appearance M.p. (uncorrected) |
|---|---|---|
| (13) | 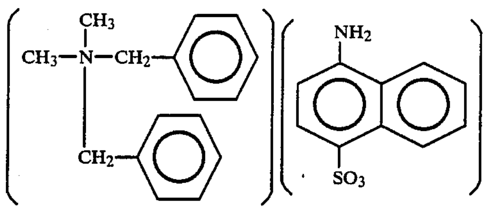 | Slightly yellow 160-165° C. |

The toner of the present invention comprises the salt forming compound of the formula (I) and at least one resin which is selected from among known resins for toners in view of adhesion, preservability, flowability, pulverizability, etc. Examples of useful resins are styrene resin, styrene-acrylic resin, styrene-butadiene resin, epoxy resin, polyester resin, paraffin wax and the like. Such resins can be used in admixture. Examples of useful coloring agents are known dyes and pigments including carbon black, lamp black, iron black, nigrosine dyes, Aniline Black, Benzidine Yellow, Hansa Yellow, chrome yellow, Rhodamine 6G Lake, quinacridone, Rose Bengale, Phthalocyanine dyes and pigments, ulramarine, triarylmethane dyes and pigments, anthraquinone dyes, monoazo and disazo dyes and pigments and the like. These coloring agents are used singly or in admixture.

When required, the toner of the present invention may further incorporate additives other than the above toner resin and coloring agent. Examples of useful additives are lubricants such as Teflon and zinc stearate, flowability imparting agents such as colloidal silica, titanium oxide and aluminum oxide, caking preventing agent, conductivity imparting agents such as carbon black and tin oxide, auxiliary fixing agents such as low-molecular-weight polyethylene, etc.

To serve as a charge control agent, the salt forming compound of the formula (I) is incorporated into the toner of the present invention in an amount of 0.1 to . 10 parts by weight, preferably 0.5 to 5 parts by weight, per 100 parts by weight of the resin.

While the toner of the present invention provides a two-component developer when admixed with a carrier, it is also of course usable as a single-component developer. The present toner is usable also as a magnetic toner when incorporating a magnetic material.

The toner of the present invention for developing electrostatic latent images can be prepared by thoroughly mixing the salt forming compound represented by the formula (I) and serving as a charge control agent, with a vinyl or non-vinyl thermoplastic resin, a pigment or dye serving as a coloring agent, and when required, a magnetic material and other additives by a ball mill or like mixer, further kneading the mixture in a molten state by a hot roll, kneader, extruder or like kneader-mixer to disperse the pigment or dye in the resulting molten mixture, solidifying the mixture by cooling and pulverizing the solid mixture, followed by classification to obtain a toner fraction having a mean particle size of 5 to 20 μm. Alternatively usable are a method wherein materials are dispersed in a resin solution, and the dispersion is spray-dried, and a method wherein specified materials are admixed with the monomers to be made into a resin to obtain an emulsified suspension, which is then polymerized to obtain a toner.

The toner of the present invention thus prepared is usable by known means for developing electrostatic latent images in electrophotography, electrostatic recording, electrostatic printing and various other applications.

The present invention will be described below in detail with reference to Examples 1 to 18 and Comparative Examples 1 to 4, in which the parts are all by weight.

EXAMPLE 1

| | |
|---|---|
| Styrene-n-butyl methacrylate copolymer resin (65/35) | 100 parts |
| Carbon black (RAVEN 1250, product of Columbia Carbon Co., Ltd.) | 7 parts |
| Compound (1) | 3 parts |

The above ingredients were uniformly mixed together by a ball mill to prepare a premix, which was then kneaded by heat rolls in a molten state, cooled, then roughly ground by a vibrating mill and further pulverized by a LABO JET (jet mill, product of Nippon Pneumatic Co., Ltd.). The fine particles obtained were classified to obtain a black toner 5 to 15 μm in particle size.

Three parts of the toner obtained was mixed with 97 parts of finely divided iron carrier (TEFV200/300, product of Nippon Teppun Co., Ltd.) to prepare a developer. The amount of initial blowoff charges of the developer was +20.3 μC/gr. The developer was used for making 10.,000 copies using a copying machine having a toner recycling device incorporated therein and was thereafter checked for the amount of blowoff charges, which was found to be +19.3 μC/gr, hence high stability.

Further when used for a commercial copying machine, the developer produced satisfactory copy images. Even after making 20,000 copies continually, there was no change in the toner image density (at least 1.50), giving good toner images without fusion (filming) of the toner to the photosensitive member.

COMPARATIVE EXAMPLE 1

A toner was prepared and then two-component developer was prepared in the same manner as in Example 1 except that Compound (1) used in Example 1 was replaced by 3 parts of BONTRON N-01 (nigrosine-type charge control agent, product of Orient Chemical Industries Ltd.).

The developer was +20.6 μC/gr in the amount of initial blowoff charges. The developer was used for the copying machine incorporating a toner recycling device for making 10,000 copies and then checked for the amount of blowoff charges, which was found to be a considerably increased value of +25.1 μC/gr. Further when used for the commercial copying machine, the developer initially produced copies of good image density (at least 1.40), but when it was used for making 10,000 copies, a reduced toner image density resulted along with fogging and filming.

EXAMPLE 2

| | |
|---|---|
| Styrene-acrylic copolymer (HIMER SMB600, product of Sanyo Kasei Co., Ltd.) | 100 parts |
| Blue pigment (Copper Phthalocyanine) | 6 parts |
| Compound (2) | 3 parts |

The above composition was made into a blue toner in the same manner as in Example 1. Three parts of the toner obtained and 97 parts of finely divided iron carrier were mixed together to prepare a developer.

The amount of initial blowoff charges of the developer was +23.6 μC/gr. When used for copying in the same manner as in Example 1, the developer produced sharp sky blue copy images free from fog. Even when used repeatedly for a prolonged period of time (10,000 copies), the developer afforded copy images free from changes.

EXAMPLE 3

A blue toner was prepared in the same manner as in Example 2 except that 3 parts of Compound(11) was used in place of Compound (2) used in Example 2.

Three parts of the toner obtained was admixed with 97 parts of finely divided iron carrier to prepare a developer. The amount of initial blowoff charges of the developer was +18.3 μC/gr. When used for copying in the same manner as in Example 1, the developer produced fog-free sharp sky blue copy images. Even after the toner was used for making 10,000 copies continually, no degradation was found in the copies obtained.

EXAMPLE 4

| | |
|---|---|
| PICCOLASTIC D-125 (styrene resin, product of Esso Petrochemical Co., Ltd.) | 100 parts |
| Biscal 550-P (polypropylene resin of low polymerization degree, product of Sanyo Kasei Co., Ltd.) | 10 parts |
| Phthalocyanine Green pigment | 10 parts |
| Compound (3) | 3 parts |

The above composition was treated in the same manner as in Example 1 to obtain a green toner. Three parts of the toner obtained was admixed with 97 parts of finely divided iron carrier to prepare a developer.

The amount of initial blowoff charges of the developer was +24.1 μC/gr. When used for copying in the same manner as in Example 1, the developer produced sharp green copy images. Even when the developer was used repeatedly for a prolonged period of time (10,000 copies), the copy images obtained were free from changes.

EXAMPLE 5

A green toner was prepared in the same manner as in Example 4 except that 3 parts of Compound (12) was used in place of Compound (3) used in Example 4.

Three parts of the toner obtained was admixed with 97 parts of finely divided iron carrier to prepare a developer. The amount of initial blowoff charges of the developer was +17.6 μC/gr. When tested by the commercial copying machine, the developer produced sharp green copy images.

EXAMPLE 6

| | |
|---|---|
| Styrene-n-butyl methacrylate copolymer resin (65/35) | 50 parts |
| Magnetite (KBC-100, product of Kanto Denka Co., Ltd.) | 45 parts |
| Carbon black (RAVEN 1250, product of Columbia Carbon Co., Ltd.) | 3 parts |
| Compound (4) | 3 parts |

The above ingredients were uniformly mixed together by a ball mill to prepare a premix, which was then kneaded by heat rolls in a molten state, cooled, then roughly ground by a continuous vibrating mill and further pulverized by a LABO JET (product of Nippon Pneumatic Co., Ltd.). The fine particles obtained were classified to prepare a single-component developer (black toner) 5 to 35 μm in particle size.

The amount of blowoff charges of the toner was +7.1 μC/gr. When tested by a commercial copying machine, the toner produced satisfactory copy images having a high density (at least 1.40) with reduced fog. The toner transfer ratio achieved was 90%.

EXAMPLE 7

| | |
|---|---|
| Styrene-2-ethylhexyl methacrylate copolymer resin (80/20) | 50 parts |
| Magnetite (KBC-100, product of Kanto Denka Co., Ltd.) | 45 parts |
| Carbon black (RAVEN 1250, product of Columbia Carbon Co., Ltd.) | 2 parts |
| Compound (10) | 3 parts |

The above composition was treated in the same manner as in Example 6 to obtain a single-component black developer (toner).

The amount of blowoff charges of the toner was +10.6 μC/gr. When tested by a commercial copying machine, the toner produced copy images of high density (at least 1.40) with reduced fog. The toner transfer ratio achieved was 90%.

EXAMPLES 8–18

Simulated toners were prepared in the same manner as in Example 1 and checked for environmental charging characteristics with lapse of time, each of the simulated toner comprising 100 parts of styrene-n-butyl methacrylate resin (65/35) and 5 parts of a compound of the invention.

Three parts of the toner was admixed with 97 parts of iron oxide beads, the mixture was placed into a polyethylene bottle, and the bottle was sealed off. The mixture was stirred by a table-type ball mill (250 r.p.m. for 20 minutes) and charged. The blowoff value was thereafter measured. The bottle was further stored in a constant-temperature constant-humidity chamber, and samples were checked for blowoff value a specified period of time later. Table 1 shows the results.

COMPARATIVE EXAMPLE 2

A toner was prepared in the same manner as in Example 8 except that 5 parts of stearyldimethylbenzylammonium-p-toluenesulfonate was used in place of 5 parts of the compound of the invention used in Example 8. The toner was similarly checked for charging characteristics. Table 1 shows the results.

COMPARATIVE EXAMPLE 3

A toner was prepared in the same manner as in Example 8 with the exception of using 5 parts of stearyldimethylbenzylammonium chloride in place of 5 parts of the present compound used in Example 8. The toner was similarly checked for charging characteristics with the results given in Table 1.

COMPARATIVE EXAMPLE 4

A toner was prepared in the same manner as in Example 8 with the exception of using 5 parts of BONTRON N-01 (nigrosine-type charge control agent, product of Orient Chemical Industries Ltd.) in place of 5 parts of the present compound. The toner was similarly checked for charging characteristics with the results given in Table 1.

TABLE 1

| | | Charging characteristics (μC/gr) | | | |
|---|---|---|---|---|---|
| Example | Compound | As prepared | Storage condition | One week later | One month later |
| 8 | (1) | 26.2 | A | 25.7 | 24.6 |
| | | | B | 25.1 | 23.6 |
| 9 | (3) | 28.6 | A | 26.2 | 25.1 |
| | | | B | 26.0 | 24.3 |
| 10 | (5) | 24.8 | A | 24.0 | 23.2 |
| | | | B | 24.1 | 23.0 |
| 11 | (6) | 25.1 | A | 24.0 | 23.1 |
| | | | B | 24.2 | 23.6 |
| 12 | (7) | 30.1 | A | 29.7 | 29.0 |
| | | | B | 29.1 | 28.0 |
| 13 | (8) | 21.3 | A | 20.8 | 19.2 |
| | | | B | 21.0 | 20.2 |
| 14 | (9) | 25.8 | A | 25.2 | 24.8 |
| | | | B | 24.9 | 23.8 |
| 15 | (10) | 24.3 | A | 24.0 | 23.6 |
| | | | B | 22.4 | 21.8 |
| 16 | (11) | 21.6 | A | 21.1 | 20.6 |
| | | | B | 20.1 | 18.6 |
| 17 | (12) | 23.7 | A | 22.6 | 22.0 |
| | | | B | 21.1 | 20.6 |
| 18 | (13) | 26.6 | A | 26.1 | 25.9 |
| | | | B | 25.8 | 25.1 |
| Comp. Ex. 2 | — | 19.6 | A | 16.2 | 14.0 |
| | | | B | 14.1 | 11.9 |
| Comp. Ex. 3 | — | 23.0 | A | 18.1 | 14.9 |
| | | | B | 15.2 | 10.2 |
| Comp. Ex. 4 | — | 20.6 | A | 20.3 | 17.0 |
| | | | B | 19.0 | 15.5 |

Note
A: 20° C., R.H. 70%
B: 50° C., R.H. 70%

Table 1 reveals that the toners of the present invention are greatly diminished in the amount of attenuation of charges at a high temperature unlike the conventional ones, thus exhibiting outstanding charging characteristics.

As stated above, the toner of the present invention containing the salt forming compound of the formula (I) as a charge control agent is uniform in the amount of triboelectric charges from particle to particle and is easily controllable in the amount of charges thereon. The toner has very high stability without undergoing variations or reduction in the amount of triboelectric charges thereon due to degradation during use, exhibits outstanding durability under various environmental conditions unlike the conventional toners and is preservable for a prolonged period of time. The toner image obtained is excellent in abrasion resistance, fixing properties and adhesion.

These outstanding advantages of the toner become more pronounced when the toner is used repeatedly for transfer copying systems wherein the charging, exposure, development and transfer steps are performed repeatedly and continuously. Further the charge control agent is less likely to adversely affect the color, so that the toner is useful for color electrophotography to produce copy images of satisfactory color.

The above set forth compounds (1) to (13) may be designated per formula (I) above as N-($C_1$–$C_8$ alkyl or benzyl)-N-($C_1$–$C_{18}$ alkyl)-N-($C_1$–$C_{18}$ alkyl)-N-($C_1$–$C_{18}$ alkyl or benzyl)-ammonium(dihydroxy, or monoamino, monohydroxy, or monoamino)-naphthalene sulfonates, and may be named as follows:

1. Benzyl-tripropyl-ammonium-1,7-dihydroxy-naphthalene-3-sulfonate,
2. Benzyl-tripropyl-ammonium-2,3-dihydroxy-naphthalene-7-sulfonate,
3. Benzyl-tributyl-ammonium-1,7-dihydroxy-naphthalene-3-sulfonate,
4. Benzyl-tributyl-ammonium-4,5-dihydroxy-naphthalene-1-sulfonate,
5. Stearyl-trimethyl-ammonium-1,7-dihydroxy-naphthalene-3-sulfonate,
6. Benzyl-octyl-dipropyl-ammonium-1,7-dihydroxy-naphthalene-3-sulfonate,
7. Dibenzyl-dimethyl-ammonium-1,7-dihydroxy-naphthalene-3-sulfonate,
8. Benzyl-tributyl-ammonium-1,5-dihydroxy-naphthalene-4-sulfonate,
9. Benzyl-tributyl-ammonium-1-hydroxy-6-amino-naphthalene-3-sulfonate,
10. Benzyl-tributyl-ammonium-4-amino-naphthalene-1-sulfonate,
11. Benzyl-tripropyl-ammonium-2-amino-naphthalene-1-sulfonate,
12. Benzyl-octyl-dimethyl-ammonium-1-amino-naphthalene-7-sulfonate, and
13. Dibenzyl-dimethyl-ammonium-4-amino-naphthalene-1-sulfonate.

What is claimed is:

1. Compound represented by the formula

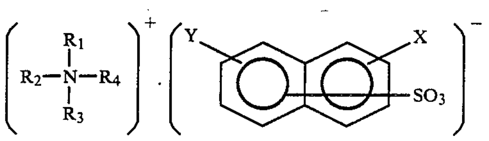

(I)

wherein $R_1$ is $C_1$–$C_8$ alkyl or benzyl, $R_2$ and $R_3$ are each $C_1$–$C_{18}$ alkyl, $R_4$ is $C_1$–$C_{18}$ alkyl or benzyl, X is hydroxyl or amino, and Y is hydroxyl or hydrogen and is not hydrogen when X is hydroxyl.

2. Compound of claim 1, wherein $R_1$ and $R_4$ are both benzyl.

3. Compound of claim 1, wherein $R_1$ is $C_1$–$C_8$ alkyl and $R_4$ is $C_1$–$C_{18}$ alkyl.

4. Compound of claim 1, wherein $R_1$ is $C_1$–$C_8$ alkyl and $R_4$ is benzyl.

5. Compound of claim 1, wherein X and Y are both Hydroxyl.

6. Compound of claim 1, wherein X is amino and Y is hydroxyl.

7. Compound of claim 1, wherein X is amino and Y is hydrogen.

8. Compound of claim 1, wherein said compound is selected from the group consisting of:

(1) Benzyl-tripropyl-ammonium-1,7 -dihydroxynaphthalene-3-sulfonate, (2) Benzyl-tripropyl-ammonium-2,3-dihydroxynaphthalene-7-sulfonate (3) Benzyl-tributyl-ammonium-1,7-dihydroxynaphthalene-1-sulfonate (4) Benzyl-tributyl-ammonium-4,5-dihydroxynaphthalene-1-sulfonate (5) Stearyl-trimethyl-ammonium-1,7-dihydroxynaphthalene-3-sulfonate (6) Benzyl-octyl-dipropyl-ammonium-1,7-dihydroxynaphthalene-3-sulfonate (7) Dibenzyl-dimethyl-ammonium-1,7-dihydroxynaphthalene-3-sulfonate (8) Benzyl-tributyl-ammonium-1,5-dihydroxynaphthalene-4-sulfonate (9) Benzyl-tributyl-ammonium-1-hydroxy-6-aminonaphthalene-3-sulfonate

(10) Benzyl-tributyl-ammonium-4-amino-naphthalenesulfonate,

(11) Benzyl-tripropyl-ammonium-2-amino-naphthalene-1-sulfonate,

(12) Benzyl-octyl-dimethyl-ammonium-1-aminonaphthalene-7-sulfonate, and

(13) Dibenzyl-dimethyl-ammonium-4-amino-naphthalene-1-sulfonate.

* * * * *